US012746350B2

(12) United States Patent
Chang et al.

(10) Patent No.: US 12,746,350 B2
(45) Date of Patent: Sep. 29, 2026

(54) ACTIVE VAPORIZATION SUCTION SYSTEM AND CONTROLLING METHOD THEREOF

(71) Applicants: Yun-Shan Chang, San Jose, CA (US); Da-Wei Lin, Taichung City (TW)

(72) Inventors: Yun-Shan Chang, San Jose, CA (US); Da-Wei Lin, Taichung City (TW)

(73) Assignees: Yun-Shan Chang, San Jose, CA (US); Da-Wei Lin, Taichung (TW)

( * ) Notice: Subject to any disclaimer, the term of this patent is extended or adjusted under 35 U.S.C. 154(b) by 750 days.

(21) Appl. No.: 18/180,824

(22) Filed: Mar. 8, 2023

(65) Prior Publication Data

US 2024/0198019 A1 Jun. 20, 2024

(30) Foreign Application Priority Data

Dec. 16, 2022 (TW) ................................. 111148585

(51) Int. Cl.
*A61M 15/00* (2006.01)

(52) U.S. Cl.
CPC ..... *A61M 15/0001* (2014.02); *A61M 2205/13* (2013.01); *A61M 2205/3592* (2013.01); *A61M 2205/8206* (2013.01); *A61M 2230/005* (2013.01); *A61M 2230/65* (2013.01)

(58) Field of Classification Search
None
See application file for complete search history.

(56) References Cited

U.S. PATENT DOCUMENTS 11,606,970 B2 * 3/2023 Fu .............................. A24F 7/00
11,723,407 B2 * 8/2023 Li ........................... A24F 40/46 131/329
2014/0060554 A1 3/2014 Collett et al.
2015/0209528 A1 7/2015 Lee et al.
2018/0043114 A1 2/2018 Bowen et al.
2019/0104768 A1 4/2019 Domenici
2019/0134324 A1 5/2019 Rabinowitz
2023/0148664 A1 * 5/2023 Hijma ..................... A24F 40/46 131/329

* cited by examiner

*Primary Examiner* — Reginald S Tillman, Jr.
(74) *Attorney, Agent, or Firm* — METIS IP LLC

(57) ABSTRACT

The present invention is an active vaporization suction system and a controlling method thereof. The system includes a medication device and an active suction device. The medication device is detachably mounted on the active suction device. When a suction module is suctioned, a flow module outputs a launching signal to a control module. The control module outputs a vaporization current control signal to a power supply module according to the launching signal. The power supply module generates and outputs a Joule vaporization current to a Joule vaporizer of the medication device according to the vaporization current control signal, so that the Joule vaporizer vaporizes a liquefied medication in a vaporization chamber into a vapor medication. In this way, when the user actively sucks the suction module, the user can take the vapor medication for medical treatment, which increases an absorption rate of the vapor medication.

9 Claims, 5 Drawing Sheets

ACTIVE VAPORIZATION SUCTION SYSTEM AND CONTROLLING METHOD THEREOF

CROSS-REFERENCE TO RELATED APPLICATION(S)

This application claims the priority benefit of TW application serial No. 111148585 filed on Dec. 16, 2022, the entirety of which is hereby incorporated by reference herein and made a part of the specification.

BACKGROUND OF THE INVENTION

1. Field of the Invention

The present invention relates to a suction system, in particular to an active vaporization suction system and a controlling method thereof.

2. Description of the Related Art

Many people in Taiwan contract a respiratory disease of different degrees since Taiwan's environment is highly humid and has drastic changes in temperature when seasons change. The respiratory diseases are, for example, nasal allergy, asthma, cough, and so on. The prior treatments comprise an oral medication, an injecting medical product, and a vaporization medication. For the vaporization medication, a vaporization device is utilized to vaporize the medication into gaseous molecules and sprays the gaseous molecules to be sucked into the nasal or the oral cavity of the user.

Since the medication is passively sucked by the user and the gaseous molecules of the medication have greater molecule volumes (usually greater than a micrometer scale), the medication cannot be determined for sure to be sucked by the user. Therefore, the user fails to determine whether the medication is sufficiently delivered to the desired to-be-cured position, such as the position of a paranasal sinus in a nose and pulmonary alveoli at an end of a bronchus. In addition, when the vaporization device continuously vaporizes the medication into gaseous molecules and sprays the gaseous molecules to air and if the gaseous molecules fail to be sucked by the user, the medication will be wasted.

SUMMARY OF THE INVENTION

In view of this, the present invention provides an active vaporization suction system and a controlling method thereof to tackle the subject.

The active aerosol suction system of the present invention comprises a medication device and an active suction device. The medication device comprises a vaporization chamber, a medication case, and a Joule vaporizer. The vaporization chamber has an inlet and an outlet. The medication case is connected to the vaporization chamber. The medication case contains a liquefied medication. The Joule vaporizer is disposed in the vaporization chamber. The medication device is detachably mounted on the active suction device. The active suction device comprises a suction module, a flow module, a control module, and a power supply module. The suction module is connected to the outlet in the vaporization chamber of the medication device. The flow module is connected to the inlet in the vaporization chamber of the medication device. The flow module detects whether the suction module is sucked. When the suction module is sucked, the flow module outputs a launching signal. The control module is electrically connected to the flow module. The power supply module is electrically connected to the control module and the Joule vaporizer in the vaporization chamber of the medication device. When the control module receives the launching signal, the control module generates and outputs a vaporization current control signal to the power supply module. The power supply module generates and outputs a vaporization current to the Joule vaporizer of the medication device according to the vaporization current control signal. The Joule vaporizer vaporizes the liquefied medication in the vaporization chamber as a vapor medication.

The present invention further provides a control method of the active aerosol suction system. The control method is performed by the control module of the active suction device, and comprises the following steps:

- determining whether a medication device is connected to the active suction device;
- when the medication device is connected to the active suction device, accessing an identity information of the medication device and validating the identity information;
- when the identity information is successfully validated, accessing at least one operation parameter;
- determining whether the flow module receives the launching signal;
- when the flow module receives the launching signal, generating and outputting a vaporization current control signal to the power supply module according to the at least one operation parameter.

The power supply module further generates and outputs the Joule vaporization current to the Joule vaporizer of the medication device according to the vaporization current control signal. The Joule vaporizer vaporizes a liquefied medication as a vapor medication.

When the user actively sucks the suction module of the present invention, the suction module generates the vapor medication for the user to suck. Since the user actively sucks the vapor medication, the vapor medication can be sucked into the deep position of the user's body desired to be cured. The vapor medication is constituted of tiny vaporization molecules, which are absorbed by alveoli and capillaries of the upper airway surgery and the lower airway surgery of the user body. Therefore, the absorbing effect of the medication is prompted. Moreover, the vapor medication is not constantly sprayed, so as to avoid wasting the vapor medication. Therefore, the treatment quality can be improved.

DETAILED DESCRIPTION OF THE INVENTION

Figure 1:
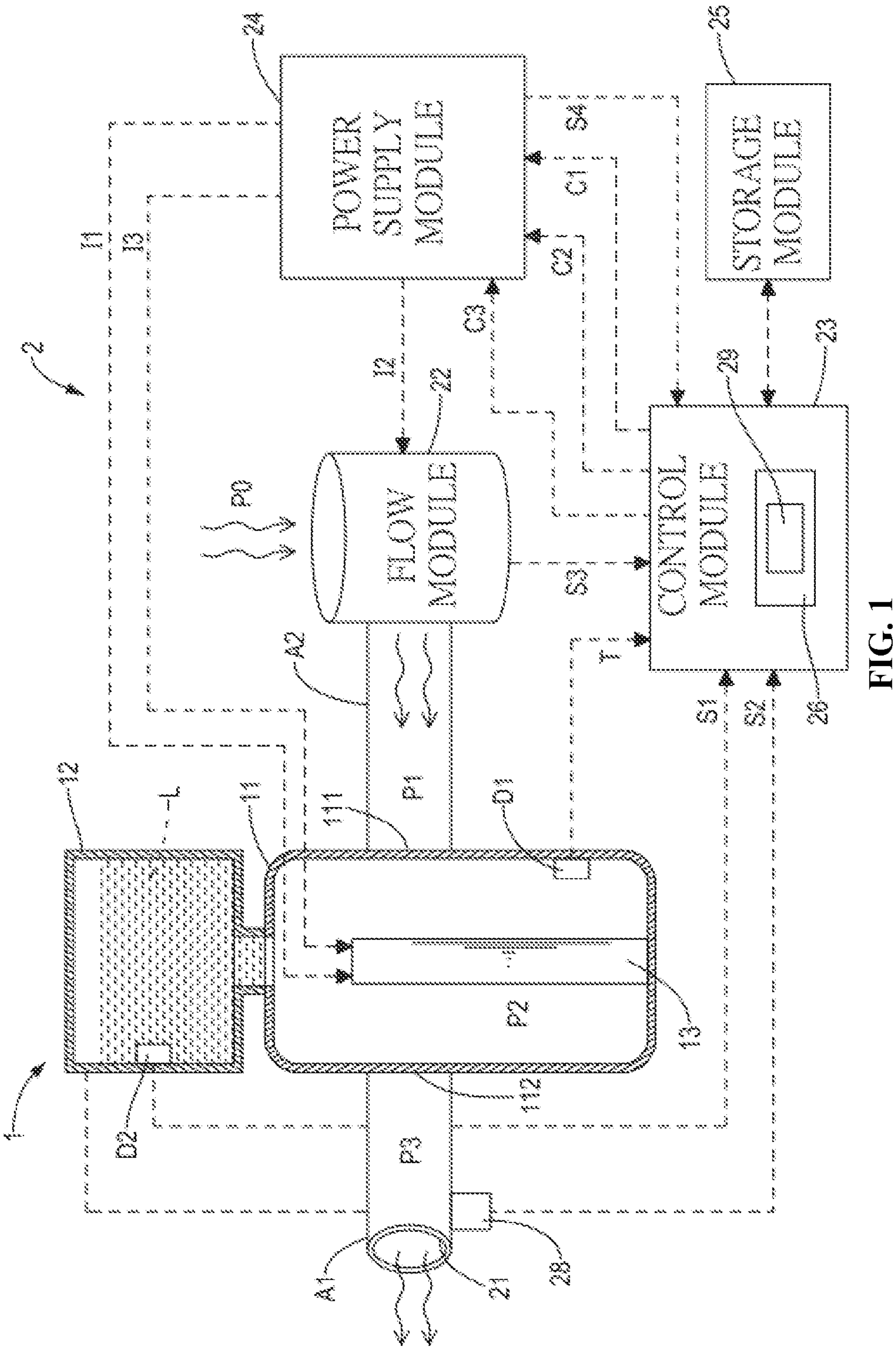
FIG. 1 is a block diagram of the active aerosol suction system of the present invention, wherein the medication device is illustrated by a sectional view.

FIG. 1 shows an active aerosol suction system of the present invention, which comprises a medication device 1 and an active suction device 2. The medication device 1 is detachably mounted on the active suction device 2. The medication device 1 comprises a vaporization chamber 11, a medication case 12, and a Joule vaporizer 13. The vaporization chamber 11 has an inlet 111 and an outlet 112. Preferably, a temperature sensor D1 is further disposed in the vaporization chamber 11. The temperature sensor D1 detects a temperature in the vaporization chamber 11 to generate a temperature signal T. The medication case 12 is connected to the vaporization chamber 11. The medication case 12 contains a liquefied medication L. The liquefied medication L can be injected into the vaporization chamber 11. Preferably, a liquid level sensor D2 is further disposed in the medication case 12. The liquid level sensor D2 detects a residual volume of the liquefied medication L in the medication case 12 to generate a residual volume signal S1.

The Joule vaporizer 13 is disposed in the vaporization chamber 11 to vaporize the liquefied medication L as a vapor medication. For instance, the Joule vaporizer 13 is a resistor. When the Joule vaporizer 13 is enabled, a vaporization state of the liquefied medication L can be adjusted according to a current passing through the Joule vaporizer. Alternatively, since the different medication devices 1 have distinct resistances of the Joule vaporizer 13, the different medication devices 1 are capable of generating distinct vaporization levels of the vapor medication. The vaporization levels of the vapor medication can be regulated according to the symptoms desired to be cured and the category of the medication.

In an embodiment of the present invention, the medication device 1 further comprises an identity certification module 28. The identity certification module 28 has an identity information. For instance, the identity certification module 28 is a recognition chip or a recognition serial number, etc. The identity information represents information of the liquefied medication L in the medication case 12. That is, the different medication devices 1 have the different identity certification modules 28 to distinguish the various liquefied medications L. When the medication device 1 is mounted on the active suction device 2, the identity information of the identity certification module 28 is accessed to generate an identification signal S2. For instance, the medication device 1 transmits the identification signal S2 via a Near-field communication (NFC) technology.

The active suction device 2 comprises a suction module 21, a flow module 22, a control module 23, and a power supply module 24. The suction module 21 is connected to the outlet 112 in the vaporization chamber 11 of the medication device 1. The flow module 22 is connected to the inlet 111 in the vaporization chamber 11 of the medication device 1. Preferably, the suction module 21 is connected to the outlet 112 via a first channel A1. The flow module 22 is connected to the inlet 111 via a second channel A2.

The suction module 21 is used to suck the vapor medication for the user. The flow module 22 detects whether the suction module 21 is sucked. When the suction module 21 is sucked, the flow module 22 outputs a launching signal S3. In detail, when the user sucks the suction module 21, the first channel A1, the vaporization chamber 11, and the second channel A2 are connected to the inner space of the flow module 22. The inner space of the second channel A2, the inner space of the vaporization chamber 11 and the inner space of the first channel A1 each respectively have a pressure P1 to P3. The pressure P1 in the second channel A2 is less than an environment pressure P0 outside the flow module 20. A pressure difference generated by the pressure P1 and the environment pressure P0 deforms a detection film in the flow module 20. The detection film is connected to an inductive coil. The inductive coil generates an inductive current. The inductive current is the launching signal S3.

The control module 23 is the process core of the control and data of the system. The control module 23 is electrically connected to the flow module 22 to receive the launching signal S3. When the control module 23 receives the launching signal S3, the control module 23 generates and outputs a vaporization current control signal C1. The power supply module 24 is electrically connected to the control module 23 and the Joule vaporizer 13 in the vaporization chamber 11. When the control module 23 outputs the vaporization current control signal C1, the power supply module 23 receives the vaporization current control signal C1 and generates and outputs a vaporization current 11 to the Joule vaporizer 13 in the vaporization chamber 11 according to the vaporization current control signal C1. The Joule vaporizer 13 vaporizes the liquefied medication L in the vaporization chamber as the vapor medication. The vaporization current control signal C1 is set according to the various liquefied medications L. When the user sucks the suction module 21, since the pressure P1 in the second channel A2 is higher than the pressure P2 in the vaporization chamber 11 and the pressure P2 in the vaporization chamber 11 is higher than the pressure P3 in the first channel A1, a sucked flow is generated from the flow module 22 to the suction module 22, and the vapor medication in the vaporization chamber 11 is exhausted with the sucked flow from the suction module 21.

In an embodiment of the present invention, the active suction device 2 further comprises a storage module 25. The storage module 25 is electrically connected to the control module 23 and stores at least one operation parameter. The at least one operation parameter is such as a vaporization parameter, a flow resistance parameter, a pre-vaporization parameter and so on. The vaporization parameter is utilized to regulate the vaporization current so that the Joule vaporizer 13 vaporizes the liquefied medication L according to various vaporization temperatures.

The control module 23 is communicatively connected to the identity certification module 28 of the medication device 1 to receive the identification signal S2, and access and validate the identity information of the identity certification module 28 according to the identification signal S2. When the identity information is successfully validated, the control module 23 accesses the operation parameter stored in the storage module 25. Therefore, whenever the operation parameter is accessed is the time when the identity information is successfully validated.

There are two validations for the identity information of the identity certification module 28, described as below.

Figure 2A:
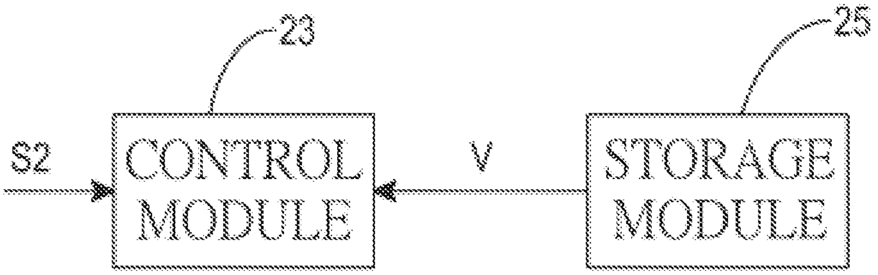
FIG. 2A is a first validation schematic diagram for the identity information of the active aerosol suction system of the present invention.

FIG. 2A is the first validation. The storage module 25 further stores an authentication information V. When the control module 23 validates the identity information, the control module 23 accesses the authentication information V stored in the storage module 25 and determines whether the identity information matches the authentication information V. When the identity information matches the authentication information V, the identity information is successfully validated.

Figure 2B:
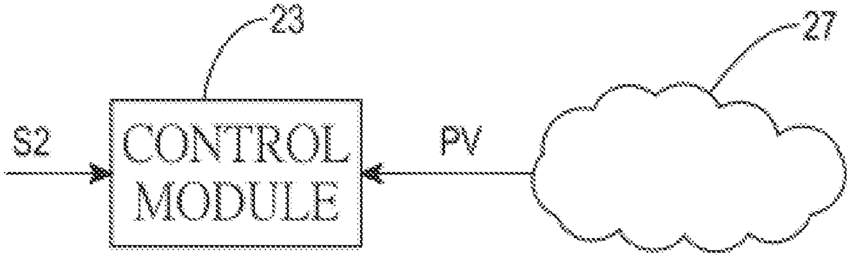
FIG. 2B is a second validation schematic diagram for the identity information of the active aerosol suction system of the present invention.

FIG. 2B is the second validation. The control module 23 is further connected to a cloud server 27. When the control module 23 validates the identity information, the control module transmits the identity information to the cloud server 27 via Internet so that the cloud server 27 validates the identity information. When the control module 23 receives an authentication completion information PV transmitted by the cloud server 27, the identity information is successfully validated.

The control module 23 is electrically connected to the temperature sensor D1 and the liquid level sensor D2 to respectively receive the temperature signal T and the residual volume signal S1. In an embodiment of the present invention, the active suction device 2 further comprises a human machine interface (HMI) 26. Preferably, the control module 23 comprises the human machine interface 26. The human machine interface 26 is utilized to set the at least one operation parameter of the system, and monitors at least one operation data of the system by a user. The operation data is generated according to the signal received by the control module 23. For example, the at least one operation data represents the temperature of the vaporization chamber 11 according to the temperature signal T. Alternatively, the at least one operation data represents a residual volume of the liquefied medication L in the medication case 12 and so on according to the residual volume signal S1.

In an embodiment of the present invention, the user sets the flow resistance parameter via the human machine interface 26. The flow resistance parameter is utilized to regulate the magnitude of the sucked flow of the flow module 22. In details, when the suction module 21 is sucked, the control module 23 outputs a flow resistance control signal C2 to the power supply module 24 according to the flow resistance parameter. The power supply module 24 outputs a flow resistance current 12 to the flow module 22 according to the flow resistance control signal C2. The flow resistance current 12 passes through a flow resistance coil of the flow module 22. The flow resistance coil generates a magnetic force according to the flow resistance current 12. The magnetic force is similar to a damping force. In brief, the flow module 22 regulates the damping force according to the flow resistance current 12. The more the flow resistance current 12 is, the larger the damping force is. The flow module 22 is difficult to be sucked for the user. The less the flow resistance current 12 is, the smaller the damping force is. Therefore, the flow module 22 is easier to be sucked for the user. In addition, the power supply module 24 outputs a power signal S4 to the control module 23. The control module 23 constantly monitors the operation of the power supply module 24 according to the power signal S4, such as an output current, an output voltage, an output temperature, and so on.

Figure 3:
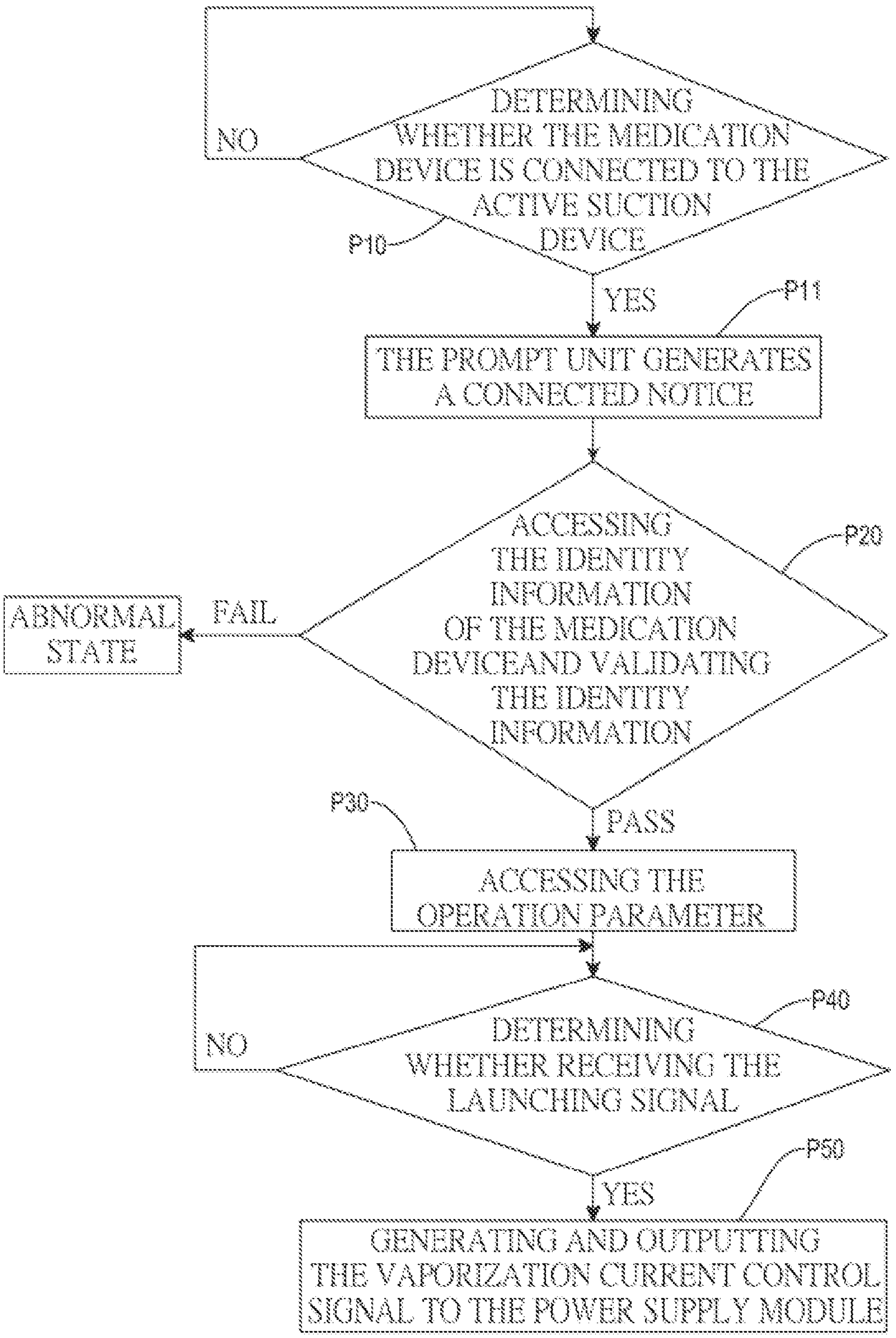
FIG. 3 is a flowchart of the control method of the active aerosol suction system of the present invention.

FIG. 3 is the flowchart of the control method for the active aerosol suction system of the present invention. The control method of the active aerosol suction system is performed by the control module 23 of the active suction device 2. The control method comprises steps P10~P50, described as below.

Step P10 is determining whether the medication device 1 is connected to the active suction device 2. For instance, the medication device 10 has a plurality of metal pins. The active suction device 2 has a plurality of metal pads corresponding to the plurality of metal pins. When the medication device 1 is mounted on the active suction device 2, the plurality of metal pins contact the plurality of metal pads. A connection signal is transmitted from the metal pins of the medication device 10 to the control module 23 via the plurality of metal pads of the active suction device 2. When the control module 23 receives the connection signal, the control module 23 determines that the medication device 1 is successfully connected to the active suction device 2.

In an embodiment of the control method of the active aerosol suction system in the present invention, there is a substep S11 between step P10 and step P20, described as below.

Step P11 is that when the medication device 1 is connected to the active suction device 2, a prompt unit 29 generates a connected notice. The connected notice is generated according to at least one of a vision effect, an audio effect, and a touch effect to notify the user that the medication device 1 is connected to the active suction device 2. The prompt unit 29 is disposed in the human machine interface 26. For instance, the prompt unit 29 is a buzzer. When the medication device 1 is connected to the active suction device 2, the prompt unit 29 generates the notice. Alternatively, the prompt unit 29 is a micro vibration motor. When the medication device 10 is connected to the active suction device 2, the prompt unit 29 generates a vibration to notify the user.

Step P20 is that when the medication device 1 is connected to the active suction device 2, the control module 23 accesses the identity information of the medication device 1 and validates the identity information. The validation method of the identity information is mentioned above and the details thereof are omitted.

Step P30 is that when the identity information is successfully validated, the control module 23 accesses the at least one operation parameter. As mentioned above, the operation parameters comprise the vaporization parameter, the flow resistance parameter, the pre-vaporization parameter and so on. The details are omitted. Since a part of the liquefied medications L need to be vaporized first, the pre-vaporization parameter is utilized to regulate a pre-vaporization temperature and a pre-vaporization period of the liquefied medication L desired to be vaporized.

In an embodiment of the control method of the active aerosol suction system in the present invention, there are substeps P31 to P34 between P30 and step P40, as shown in FIG. 3, described as below.

Step P31 is that the control module 23 determines whether the liquefied medication L needs to be vaporized first according to the identity information. Since the identity information represents the category of the liquefied medication L in the medication device, the user builds a pre-vaporization list in the storage module 25 or in the cloud server 27. The pre-vaporization list comprises multiple identity information desired to be vaporized first. When the control module 23 validates the identity information, that is, simultaneously determines whether the liquefied medication L corresponding to the identity information needs to be vaporized first.

Step P32 is that when the liquefied medication L needs to be vaporized, the control module 23 generates and outputs a pre-vaporization current control signal C3 to the power supply module 24 according to the pre-vaporization parameter. The power supply module 24 generates and outputs a pre-vaporization current 13 to the Joule vaporizer 13 according to the pre-vaporization current control signal. The temperature in the vaporization chamber 11 will rise and the control module 23 determines whether the temperature in the vaporization chamber 11 reaches a pre-vaporization temperature via constantly monitoring the temperature signal T.

Step P33 is that the control module 23 determines whether the temperature in the vaporization chamber 11 reaches a pre-vaporization temperature. If yes, the control module 23 turns off the Joule vaporizer 13. If not, the control method returns to substep P32. The control module 23 determines whether the temperature in the vaporization chamber 11 reaches a pre-vaporization temperature via constantly monitoring the temperature signal T.

Step P40 is determining whether the control module 23 receives the launching signal S3. In brief, when the user sucks the suction module 21, the flow module 22 generates and outputs the launching signal S3 to the control module 23. When the control module 23 receives the launching signal S3, determining the suction module 21 is sucked; otherwise the suction module 21 fails to be sucked.

Step P50 is that when the control module 23 receives the launching signal S3, the control module 23 generates and outputs the vaporization current control signal C1 to the power supply module 24 according to the operation parameter. The power supply module 24 generates and outputs the vaporization current 11 to the Joule vaporizer 13 of the medication device 1 according to the vaporization current control signal C1. The Joule vaporizer 13 vaporizes the liquefied medication L as a vapor medication.

Figure 4:
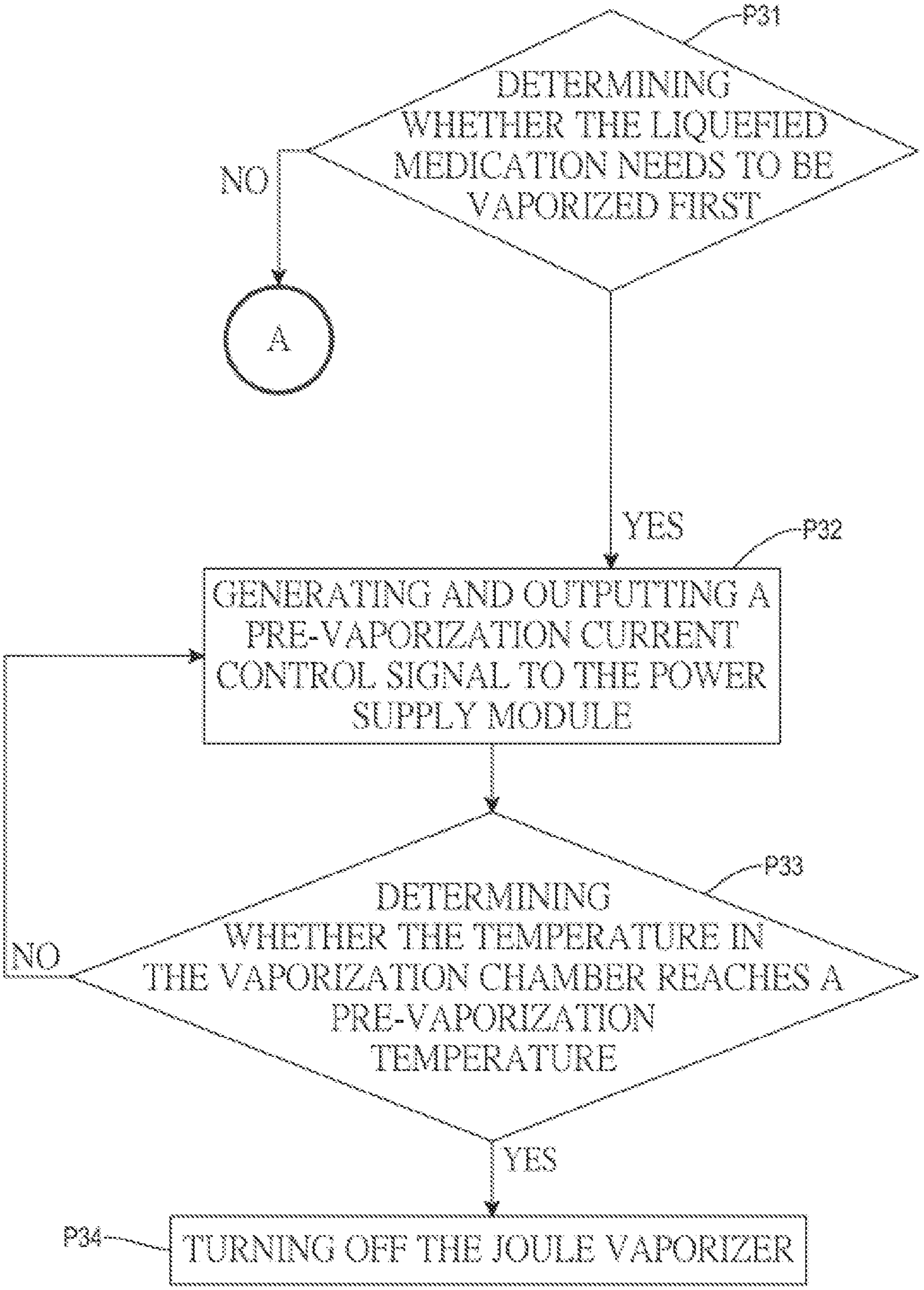
FIG. 4 is a substep flowchart of step P30 in the control method of the active aerosol suction system of the present invention.
Figure 5:
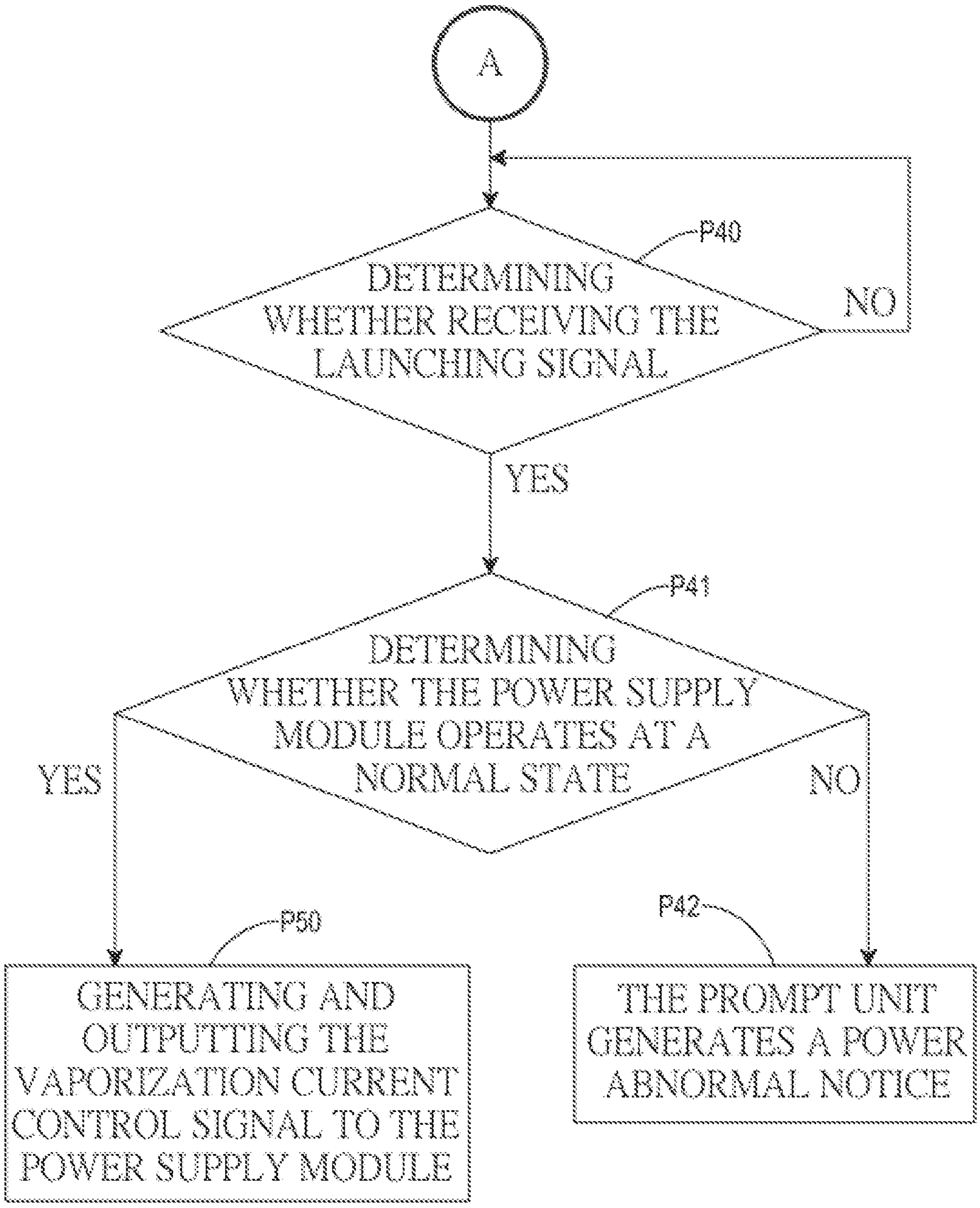
FIG. 5 is a substep flowchart of step P40 in the control method of the active aerosol suction system of the present invention.

In an embodiment of the control method active aerosol suction system in the present invention, there are substeps P41~P42 between step P40 and step P50, as shown in FIG. 4 and described as below.

Step P41 is that the control module 23 determines whether the power supply module 24 operates at a normal state, that is, whether the power supply module 24 provides electric power steadily. The control module 23 determines whether the power supply module 24 provides electric power steadily according to the power signal S4. For instance, when the power supply module 24 provides electric power to a battery, the power signal S4 represents a residual energy. When the residual energy of the battery is insufficient, the control module 30 determines that the power supply module 40 fails to provide electric power steadily, that is, the power supply module 24 operates at an abnormal state.

Step P42 is that when the power supply module 40 fails to provide electric power steadily, the prompt unit 29 generates a power abnormal notice. The details are mentioned above and omitted hereinafter.

When the user actively sucks the suction module of the present invention, the suction module generates the vapor medication for the user to suck. Since the user actively sucks the vapor medication, the vapor medication can be sucked into the deep position of the user's body desired to be cured. The vapor medication is constituted of tiny vaporization molecules, which are absorbed by alveoli and capillaries of the upper airway surgery and the lower airway surgery of the user body. Therefore, the absorbing effect of the medication is prompted. Moreover, the vapor medication is not constantly sprayed, so as to avoid wasting the vapor medication. Therefore, the treatment quality can be improved.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. An active aerosol suction system, comprising:

a medication device, comprising:

a vaporization chamber, having an inlet and an outlet;

a medication case, connected to the vaporization chamber, and the medication case containing a liquefied medication;

a Joule vaporizer, disposed in the vaporization chamber;

an identity certification module, having an identity information;

an active suction device, the medication device detachably mounted on the active suction device, and the active suction device comprising:

a suction module, connected to the outlet of the vaporization chamber in the medication device;

a flow module, connected to the inlet of the vaporization chamber in the medication device; wherein the flow module detects whether the suction module is sucked, and when the suction module is sucked, the flow module outputs a launching signal;

a control module, electrically connected to the flow module;

a power supply module, electrically connected to the control module and the Joule vaporizer in the vaporization chamber of the medication device;

wherein when the control module receives the launching signal, the control module generates and outputs a vaporization current control signal to the power supply module so that the power supply module generates and outputs a vaporization current to the Joule vaporizer of the medication device according to the vaporization current control signal, and the Joule vaporizer vaporizes the liquefied medication in the vaporization chamber as a vapor medication;

a storage module, electrically connected to the control module and storing at least one operation parameter:

wherein when the medication device is mounted on the active suction device, the control module of the active suction device is further communicatively connected to the identity certification module of the medication device and the control module accesses and validates the identity information;

wherein when the identity information is successfully validated, the control module accesses the operation parameter stored in the storage module;

wherein when the flow module receives the launching signal, the control module generates and outputs the vaporization current control signal to the power supply module according to the launching signal and the at least one operation parameter.

2. The active aerosol suction system of claim 1, wherein the active suction device further comprises a human machine interface, utilized to set the at least one operation parameter and monitor at least one operation data by a user.

3. The active aerosol suction system of claim 1, wherein the storage module further stores an authentication information;

wherein when the control module validates the identity information, the control module accesses the authentication information stored in the storage module and determines whether the identity information matches the authentication information;

wherein when the identity information matches the authentication information, the identity information is successfully validated.

4. The active aerosol suction system of claim 1, wherein when the control module validates the identity information, the control module transmits the identity information to a cloud server via Internet so that the cloud server validates the identity information;

wherein when the control module receives an authentication completion information transmitted by the cloud server, the identity information is successfully validated.

5. A control method of an active aerosol suction system, executed by a control module of an active suction device, the control method comprising steps as follows:

determining whether a medication device is connected to the active suction device;

when the medication device is connected to the active suction device, accessing an identity information of the medication device and validating the identity information;

when the identity information is successfully validated, accessing at least one operation parameter;

determining whether a flow module receives a launching signal;

when the flow module receives the launching signal, generating and outputting a vaporization current control signal to a power supply module according to the at least one operation parameter such that the power supply module generates and outputs a vaporization current to a Joule vaporizer of the medication device according to the vaporization current control signal, and the Joule vaporizer vaporizes a liquefied medication as a vapor medication.

6. The control method of the active aerosol suction system of claim 5, wherein the at least one operation parameter comprises:

a vaporization parameter, controlling the vaporization current;

a flow resistance parameter, controlling a suction force of a flow module; and a pre-vaporization parameter, controlling a pre-vaporization current.

7. The control method of the active aerosol suction system of claim 5, wherein between step (a) and step (b) the control method further comprises a substep:

(a1) when the medication device is connected to the active suction device, generating a connected notice according to at least one of a vision effect, an audio effect, and a touch effect by a prompt unit.

8. The control method of the active aerosol suction system of claim 5, wherein between step (c) and (d) the control method further comprises a substep:

(c1) determining whether the liquefied medication needs to be pre-vaporized according to the identity information;

(c2) when the liquefied medication needs to be pre-evaporized, the control module generates and outputs a pre-vaporization current control signal to the power supply module according to the at least one operation parameter and the power supply module generates and outputs a pre-vaporization current to the Joule vaporizer according to the pre-vaporization current control signal.

9. The control method of the active aerosol suction system of claim 5, wherein between step (d) and step (e) the control method further comprises a substep:

(d1) determining whether the power supply module is at a power normal state;

(d2) when the power supply module is not at the power normal state, generating a power abnormal notice by a prompt unit.

* * * * *